United States Patent
Komorowski

(10) Patent No.: US 10,363,222 B2
(45) Date of Patent: *Jul. 30, 2019

(54) MULTIPLE UNIT DOSAGE FORM HAVING A THERAPEUTIC AGENT IN COMBINATION WITH A NUTRITIONAL SUPPLEMENT

(71) Applicant: JDS Therapeutics, LLC, Purchase, NY (US)

(72) Inventor: James R Komorowski, Trumbull, CT (US)

(73) Assignee: JDS Therapeutics, LLC, Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/215,979

(22) Filed: Jul. 21, 2016

(65) Prior Publication Data

US 2016/0324784 A1  Nov. 10, 2016

Related U.S. Application Data

(63) Continuation of application No. 14/642,243, filed on Mar. 9, 2015, now Pat. No. 9,421,170, which is a
(Continued)

(51) Int. Cl.
*A61K 9/24* (2006.01)
*A61K 9/00* (2006.01)
(Continued)

(52) U.S. Cl.
CPC .............. *A61K 9/209* (2013.01); *A23L 33/15* (2016.08); *A61K 9/00* (2013.01); *A61K 9/0053* (2013.01);
(Continued)

(58) Field of Classification Search
CPC ........ A61K 9/209; A61K 9/00; A61K 9/0053; A61K 45/06; A61K 31/155; A23L 33/15; A23V 2002/00
See application file for complete search history.

(56) References Cited

U.S. PATENT DOCUMENTS

| 3,939,259 A | 2/1976 | Pescetti |
| 3,965,256 A | 6/1976 | Leslie |

(Continued)

FOREIGN PATENT DOCUMENTS

| CN | 1665566 | 9/2005 |
| CN | 1823608 | 8/2006 |

(Continued)

OTHER PUBLICATIONS

Alberti, et al: "Definition, Diagnosis and Classification of Diabetes Mellitus and it's Complications Part 1: Diagnosis and Classification of Diabetes Mellitus Provisional Report of a WHO Consultation", *Diabet Med* 15: 539 (1998).
(Continued)

*Primary Examiner* — Blessing M Fubara
(74) *Attorney, Agent, or Firm* — Porzio, Bromberg & Newman P.C.

(57) ABSTRACT

Compositions and methods for combination therapy are provided. The compositions comprise a multiple unit dosage form having both a therapeutic agent and a nutritional supplement. The combination therapy is useful for restoring a nutrient depletion associated with a particular disease state. Additionally, the combination therapy can prevent or attenuate the depletion of a nutrient caused, in whole or in part, by the co-administrated therapeutic drug. Methods of manufacturing the formulations are likewise described.

22 Claims, 2 Drawing Sheets

Related U.S. Application Data continuation of application No. 13/857,813, filed on Apr. 5, 2013, now Pat. No. 9,005,637, which is a continuation of application No. 12/645,124, filed on Dec. 22, 2009, now Pat. No. 8,586,061, which is a continuation of application No. PCT/US2008/067736, filed on Jun. 20, 2008.

(60) Provisional application No. 60/946,357, filed on Jun. 26, 2007.

(51) Int. Cl.
 A61K 31/155 (2006.01)
 A61K 45/06 (2006.01)
 A23L 33/15 (2016.01)

(52) U.S. Cl.
 CPC ............ *A61K 31/155* (2013.01); *A61K 45/06* (2013.01); *A23V 2002/00* (2013.01)

(56) References Cited

U.S. PATENT DOCUMENTS

| | | | |
|---|---|---|---|
| 4,164,573 A | 8/1979 | Galinsky | |
| 4,315,927 A | 2/1982 | Evans | |
| 4,421,685 A | 12/1983 | Chance et al. | |
| 4,424,057 A | 1/1984 | Arcse | |
| 4,476,118 A | 10/1984 | Brange et al. | |
| 4,571,391 A | 2/1986 | Riley et al. | |
| 4,954,492 A | 9/1990 | Jensen | |
| 5,023,252 A | 6/1991 | Hseih | |
| 5,053,389 A | 10/1991 | Balschmidt et al. | |
| 5,057,320 A | 10/1991 | Evans et al. | |
| 5,085,996 A | 2/1992 | Evans | |
| 5,087,623 A | 2/1992 | Boynton | |
| 5,087,624 A | 2/1992 | Boynton | |
| 5,093,200 A | 3/1992 | Watanabe et al. | |
| RE33,988 E | 7/1992 | Evans | |
| 5,164,384 A | 11/1992 | Paul | |
| 5,175,156 A | 12/1992 | Boynton et al. | |
| 5,194,615 A | 3/1993 | Jensen | |
| 5,320,853 A | 6/1994 | Noda | |
| 5,336,672 A | 8/1994 | Southern, Jr. et al. | |
| 5,474,978 A | 12/1995 | Bakaysa et al. | |
| 5,496,827 A | 3/1996 | Patrick | |
| 5,534,488 A | 7/1996 | Hoffmann | |
| 5,582,839 A | 12/1996 | McCarty | |
| 5,597,585 A | 1/1997 | Williams et al. | |
| 5,631,288 A | 5/1997 | De Simone | |
| 5,635,535 A | 6/1997 | Wagstaff | |
| 5,643,957 A | 7/1997 | Leone-Bay et al. | |
| 5,650,386 A | 7/1997 | Leone-Bay et al. | |
| 5,707,970 A | 1/1998 | McCarty et al. | |
| 5,721,114 A | 2/1998 | Abrahamsen et al. | |
| 5,731,303 A | 3/1998 | Hsieh | |
| 5,766,633 A | 6/1998 | Milstein et al. | |
| 5,773,647 A | 6/1998 | Leone-Bay et al. | |
| 5,776,498 A | 7/1998 | McCarty | |
| 5,776,504 A | 7/1998 | McCarty | |
| 5,776,888 A | 7/1998 | Leone-Bay et al. | |
| 5,789,401 A | 8/1998 | McCarty | |
| 5,804,688 A | 9/1998 | Leone-Bay et al. | |
| 5,858,968 A | 1/1999 | Weiner et al. | |
| 5,863,944 A | 1/1999 | Leone-Bay et al. | |
| 5,866,536 A | 2/1999 | Leone-Bay et al. | |
| 5,876,710 A | 3/1999 | Leone-Bay et al. | |
| 5,876,757 A | 3/1999 | McCarty | |
| 5,879,681 A | 3/1999 | Leone-Bay et al. | |
| 5,914,326 A | 6/1999 | McCarty et al. | |
| 5,929,066 A | 7/1999 | McCarty | |
| 5,939,381 A | 8/1999 | Leone-Bay et al. | |
| 5,955,503 A | 9/1999 | Leone-Bay et al. | |
| 5,965,121 A | 10/1999 | Leone-Bay et al. | |
| 5,989,539 A | 11/1999 | Leone-Bay et al. | |
| 5,990,166 A | 11/1999 | Leone-Bay et al. | |
| 6,001,347 A | 12/1999 | Leone-Bay et al. | |
| 6,004,925 A | 12/1999 | Dasseux et al. | |
| 6,037,323 A | 3/2000 | Dasseux et al. | |
| 6,048,846 A | 4/2000 | Cochran | |
| 6,051,561 A | 4/2000 | Leone-Bay et al. | |
| 6,060,513 A | 5/2000 | Leone-Bay et al. | |
| 6,071,510 A | 6/2000 | Leone-Bay et al. | |
| 6,090,958 A | 7/2000 | Leone-Bay et al. | |
| 6,099,869 A | 8/2000 | McCarty | |
| 6,100,298 A | 8/2000 | Leone-Bay et al. | |
| 6,140,304 A | 10/2000 | Sears | |
| 6,156,735 A | 12/2000 | McCarty et al. | |
| 6,203,823 B1 | 3/2001 | McCarty | |
| 6,251,889 B1 | 6/2001 | de la Harpe et al. | |
| 6,329,361 B1 | 12/2001 | McCarty | |
| 6,344,444 B1 | 2/2002 | McCarty et al. | |
| 6,358,504 B1 | 3/2002 | Leone-Bay et al. | |
| 6,376,549 B1 | 4/2002 | Fine et al. | |
| 6,576,233 B2 | 6/2003 | Hsia et al. | |
| 6,689,383 B1 | 2/2004 | Anderson et al. | |
| 6,809,115 B2 | 10/2004 | Katz et al. | |
| 7,112,561 B2 | 9/2006 | Gyurik et al. | |
| RE39,480 E | 1/2007 | McCarty | |
| 7,291,591 B2 | 11/2007 | Fishman | |
| 7,429,564 B2 | 9/2008 | Arbit et al. | |
| 8,062,677 B2 | 11/2011 | Komorowski | |
| 8,586,061 B2 * | 11/2013 | Komorowski | A61K 9/209 424/400 |
| 8,933,022 B2 | 1/2015 | Komorowski | |
| 9,005,637 B2 * | 4/2015 | Komorowski | 424/400 |
| 9,421,170 B2 * | 8/2016 | Komorowski | A61K 9/209 |
| 2001/0055645 A1 * | 12/2001 | Flook | A23L 2/02 426/599 |
| 2002/0081315 A1 | 6/2002 | Katz et al. | |
| 2002/0098247 A1 | 7/2002 | Komorowski et al. | |
| 2002/0197331 A1 | 12/2002 | Komorowski et al. | |
| 2003/0091654 A1 | 5/2003 | Katz et al. | |
| 2003/0211172 A1 | 11/2003 | Jones et al. | |
| 2004/0005368 A1 | 1/2004 | Mann et al. | |
| 2004/0043065 A1 | 3/2004 | Stankov | |
| 2004/0115265 A1 * | 6/2004 | Benkerrour | A61K 9/209 424/471 |
| 2004/0185119 A1 * | 9/2004 | Theuer | A61K 31/375 424/682 |
| 2005/0058704 A1 | 3/2005 | Schneider et al. | |
| 2005/0069593 A1 | 3/2005 | Zwiefel | |
| 2005/0214384 A1 | 9/2005 | Juturu et al. | |
| 2005/0214385 A1 | 9/2005 | Komorowski et al. | |
| 2005/0226845 A1 * | 10/2005 | Liu | A61K 38/21 424/85.4 |
| 2005/0233946 A1 | 10/2005 | Fine et al. | |
| 2006/0024383 A1 * | 2/2006 | Berlin | A61K 31/045 424/655 |
| 2006/0088574 A1 | 4/2006 | Manning et al. | |
| 2006/0204505 A1 * | 9/2006 | Sliwkowski | C07K 16/32 424/155.1 |
| 2006/0234913 A1 * | 10/2006 | Arbit | A61K 9/2013 514/1.9 |
| 2007/0092584 A1 | 4/2007 | Fine et al. | |
| 2008/0160106 A1 * | 7/2008 | Fais | A61K 31/4439 424/687 |
| 2009/0155384 A1 | 6/2009 | Komorowski | |
| 2010/0009015 A1 | 1/2010 | Juturu et al. | |
| 2010/0262434 A1 | 10/2010 | Shaya | |
| 2012/0100228 A1 | 4/2012 | Komorowski | |
| 2012/0128794 A1 | 5/2012 | Komorowski | |
| 2012/0225134 A1 | 9/2012 | Komorowski | |
| 2015/0094258 A1 | 4/2015 | Komorowski | |
| 2015/0272991 A1 | 10/2015 | Juturu et al. | |
| 2015/0320796 A1 | 11/2015 | Komorowski | |
| 2015/0320874 A1 | 11/2015 | Komorowski | |

FOREIGN PATENT DOCUMENTS

| | | |
|---|---|---|
| DK | 135268 | 2/1974 |
| EP | 0 016 496 | 10/1980 |
| EP | 0 598 309 | 5/1994 |
| EP | 0 881 649 | 12/1998 |

(56) References Cited

FOREIGN PATENT DOCUMENTS

| | | |
|---|---|---|
| EP | 1 731 142 | 12/2006 |
| IN | 2004MU01120 | 1/2007 |
| WO | WO 91/11117 | 8/1991 |
| WO | WO 95/28838 | 11/1995 |
| WO | WO 96/25939 | 8/1996 |
| WO | WO 96/35421 | 11/1996 |
| WO | WO 98/25589 | 6/1998 |
| WO | WO 99/07387 | 2/1999 |
| WO | WO 00/06534 | 2/2000 |
| WO | WO 00/07979 | 2/2000 |
| WO | WO 00/12095 | 3/2000 |
| WO | WO 00/15211 | 3/2000 |
| WO | WO 00/47188 | 8/2000 |
| WO | WO 00/50386 | 8/2000 |
| WO | WO 00/59863 | 10/2000 |
| WO | WO 01/19542 | 3/2001 |
| WO | WO 01/21073 | 3/2001 |
| WO | WO 01/25679 | 4/2001 |
| WO | WO 01/25704 | 4/2001 |
| WO | WO 01/32130 | 5/2001 |
| WO | WO 01/32596 | 5/2001 |
| WO | WO 01/34114 | 5/2001 |
| WO | WO 01/41985 | 6/2001 |
| WO | WO 01/44199 | 6/2001 |
| WO | WO 01/51454 | 7/2001 |
| WO | WO 02/02509 | 1/2002 |
| WO | WO 02/04024 | 1/2002 |
| WO | WO 02/11564 | 2/2002 |
| WO | WO 02/19969 | 3/2002 |
| WO | WO 02/20466 | 3/2002 |
| WO | WO 02/24180 | 3/2002 |
| WO | WO 02/36127 | 5/2002 |
| WO | WO 02/36202 | 5/2002 |
| WO | WO 02/67953 | 9/2002 |
| WO | WO 02/69937 | 9/2002 |
| WO | WO 02/70438 | 9/2002 |
| WO | WO 03/43569 | 5/2003 |
| WO | WO 03/90671 | 11/2003 |
| WO | WO 04/107881 | 12/2004 |
| WO | WO 06/060753 | 6/2006 |
| WO | WO 07/016256 | 2/2007 |
| WO | WO 08/094939 | 8/2008 |
| WO | WO 08/112706 | 9/2008 |
| WO | WO 2009/002867 | 12/2008 |
| WO | WO 11/002939 | 1/2011 |
| WO | WO 12/119007 | 9/2012 |

OTHER PUBLICATIONS

Anderson, Chromium Metabolism and Its Role in Disease, Processes in Man, Clin. Psychol. Biochem., 1986, 4:31-41.
Anderson et al., 1987, Effects of supplemental chromium on patients with symptoms of reactive hypoglycemia, Metabolism, 36(4):351-355.
Anderson et al., Lack of Toxicity of Chromium Chloride and Picolinate, 16 J. Am. Coll. Nutr. 1997, pp. 273-279.
Anderson, Richard A., Nutritional Factors Influencing the Glucose/Insulin System: Chromium, Journal of the American College of Nutrition, 1997, 16(5):404-410.
Anderson, Richard A. et al., Stability and Absorption of Chromium and Absorption of Chromium Histidinate Complexes by Humans, Biological Trace Element Research, 2004, 101:211-218.
Aragno et al., 2002, Dehydroepiandrosterone modulates nuclear factor-kB activation in hippocampus of diabetic rats, Endocrinology, 143(9):3250-3258.
Bailey, M .M. et al., "Exposure of pregnant mice to chromium picolinate results in skeletal defects in their offspring", Birth Defects Research Part B: Developmental and Reproductive Toxicology, 77: 244-249 (2006).
Badimon et al., "Role of high density lipoproteins in the regression of atherosclerosis", Circulation 86: (Suppl. III) 86-94 (1992).
Berge et al., "Pharmaceutical Salts", Journal of Pharmaceutical Sciences, pp. 1-19, vol. 66, No. 1 (1977).
Boyle et al., Chromium depletion in the pathogenesis of diabetes and atherosclerosis, Southern Med. J. 70:1449-1453 (1977).
Bridges, Apr. 19, 2001, Iron deficiency, Encyclopedia of Life Sciences, p. 1-8 (Online).
Brun et al. "Synapse Loss and Gliosis in the Molecular Layer of the Cerebral Cortex in Alzheimer's Disease and in Frontal Lobe Degeneration", (1995) *Neurodegeneration* 4:171.
Campbell et al., 1962, Interaction of insulin and chromium (III) on mitochondrial swelling, Am. J. Physiol, 204(6):1028-1030.
Castro et al., "Cardiometabolic Syndrome: Pathophysiology and Treatment", Curr Hypertens Rep. 5(5):393-401 (2003).
Cefalu, William T. et al., "The Effect of Chromium Supplementation on Carbohydrate Metabolism and Body Fat Distribution" Diabetes, p. 55A, vol. 46 (1997).
Christman et al., 2000, Redox regulation of nuclear factor Kappa B: therapeutic potential for attenuating inflammatory responses, Brain Pathology, 10:153-162.
"Chrom bei Diabetes mellitus", (Oct. 31, 2010), Retrieved from the Internet: http://web.archive.org/web/28181831894 712/http://www.diabetiker-experte.de/Chrom-bei-Diabetes-mellitus.html, 3 pp.
Cornford et al. "High Expression of the Glut1 Glucose Transporter in Human Brain Hemangioblastoma Endothelium", (1998) *J. Neuropathol. Exp. Neurol.* 54:842-851.
Cornford, et al. "Dynamic [$^{18}$F]Fluorodeoxyglucose Positron Emission Tomography and Hypometabolic Zones in Seizures: Reduced Capillary Influx", (1998) *Ann. Neurol.* 43:801-808.
Dansky and Fisher, "High-Density Lipoprotein and Plaque Regression: The Good Cholesterol Gets Even Better", Circulation 100:1762-3 (1999).
Davis et al., "Effects of Over-the-Counter Drugs on Chromium Retention and Urinary Excretion in Rats", J. Nutrition Res. 15:202-210 (1995 ).
Diem, et al., "Scientific Tables" Documenta Geigy, Seventh Edition, pp. 457-497 (1975).
Diplock, "Antioxidant Nutrients and Disease Prevention: An Overview" Am. J. Clin. Nutr., pp. 189-193, vol. 53 (1991).
Dousset et al., 2001, Trace elements, free radicals, and Hiv progression, Nutrition and AIDS, 2nd ed. CRC Press, Chapter 4, pp. 23-20.
Dorflinger, L.J., "Metabolic Effects of Implantable Steroid Contraceptives for Women", Contraception 65:47-62 (2002).
Drake et al. "Chromium Infusion in hospitalized patients with severe insulin resistance: a retrospective analysis." Endocr Pract. Jan. 31, 2012:1-17 [Epub ahead of print].
Evans, et al., "Chromium Picolinate Increases Membrane Fluidity and Rate of Insulin Internalization" Journal of Inorganic Biochemistry, 46:243-250 (1992).
Feng et al., 2002, Chromium picolinate reduces insulin requirement in people with type 2 diabetes mellitus, Diabetes. 1929-PO, A469 (2002 Annual Conference).
Fielding and Fielding, "Molecular Physiology of Reverse Cholesterol Transport", J Lipid Res. 36:211-228 (1995).
Gamberino et al. "Glucose Transporter Isoform Expression in Huntington's Disease Brain", (1994) *J. Neurochem.* 63:1392-1397.
Golik et al., 1998, Effects of captopril and enalapril on zinc metabolism in hypertensive patients, Journal of the American College of Nutrition, 17(1):75-78.
Gress et al., "Hypertension and Antihypertensive Therapy as Risk Factors for Type 2 Diabetes Mellitus", N. Eng. J. Med. 342:905-912 (2000).
Govindaraju et al., "Chromium(III)-Insulin Derivatives and Their Implication in Glucose Metabolism", Journal of Inorganic Biochemistry, 35:137-147 (1989).
Govindaraju et al., "Chymotrypsin-Catalyzed Hydrolysis of Chromium(III) Derivatives of Insulin: Evidence for Stabilization of the Protein Through Interactions with Metal Ions", Journal of Inorganic Biochemistry, 35:127-135 (1989).
Hannonen et al. "Neurocognitive functioning in children with type-1 diabetes with and without episodes of severe hypoglycaemia", (2003) *Developmental Medicine & Child Neurology* 45:4:262-268.
Hayden and Ma, "Molecular Genetics of Human Lipoprotein Lipase Deficiency", Mol. Cell Biochem. 113:171-176 (1992).
Hou et al., Chin Med J (Engl). 120(19):1704-1709 (2007).

(56) References Cited

OTHER PUBLICATIONS

Jula et al., "Effects of Diet and Simvastatin on Serum Lipids, Insulin, and Antioxidants in Hypercholesterolemic Men", JAMA 287:598-605, 604 (2002).
Julius et al., "Antihypertensive Treatment of Patients with Diabetes and Hypertension", Am. J. Hypertens. 14:310S-316S, 313S (2001).
Juturu, "Cardiometabolic Syndrome—New Therapeutic Challenges", DPG Medical Nutrition Matters 26(2):1, 3-10 (2006).
Juturu, et al., "Absorption and excretion of chromium from orally administered chromium chloride, chromium acetate and chromium oxide in rats" Trace Elements and Electrolytes, 20(1):23-28, (2003).
Kalaria et al. "Reduced Glucose Transporter at the Blood-Brain Barrier and in Cerebral Cortex in Alzheimer Disease", (1989) J. Neurochem. 53:1083-1088.
Kamath et al., Absorption, Retention and Urinary Excretion of Chromium-51 in Rats Pretreated with Indomethacin and Dosed with Dimethylprostaglandin E2, Misoprostol or Prostacyclin, J. Nutrition 127:478-482 (1997).
Katsumata et al. "Suboptimal energy balance selectively up-regulates muscle GLUT gene expression but reduces insulin-dependent glucose uptake during postnatal development", (1999) FASEB J. 11:1405-13.
Kim et al., 2001, Molecular targets of selenium in cancer prevens= tion, Nutrition and Cancer, 40(1):50-54.
Koivisto et al., Mar. 1999, Lispro Mix25 insulin as premeal therapy in type 2 diabetic patients, Diabetes Care, 22(3):459-462.
Komorowski et al., 2011, Chromium histidinate reduces brain damage caused by insulin-induced hypoglycemia, The FASEB Journal, 25:766.13 (Abstract).
Lastra et al., "Cardiometabolic Syndrome and Chronic Kidney Disease", Curr Diab Rep. 6(3):207-12 (2006).
Lindemann, et al., "Effect of chromium source on tissue concentration of chromium in pigs" J Anim Sci, 86: 2971-2978 (2008).
Markesbery et al. "Oxidative Alterations in Alzheimer's Disease", (1999) Brain Pathol 9(1):133-46.
Martin, et al., Aug. 2006, Chromium picolinate supplementation attenuates body weight gain and increases insulin sensitivity in subjects with type 2 diabetes, Diabetes Care, 29(8):1826-32.
Mazziotta, et al. "Reduced Cerebral Glucose Metabolism in Asymptomatic Subjects At Risk for Huntington's Disease", (1987) New England J. Med. 316:357-362.
McCarty, Mark F. "The Case for Supplemental Chromium and A Survey of Clinical Studies With Chromium Picolinate", Journal of Applied Nutrition, 43(1):58-66 (1991).
Melki et al., 1993, Expression of the adipocyte fatty acid-binding protein in streptozotocin-diabetes: effects of insulin deficiency and supplementation, Journal of Lipd Research 34:1527-1534.
Miranda, et al., "Effect of Chromium and Zinc on Insulin Signaling in Skeletal Muscle Cells" Biological Trace Element Research, 101:19-36, vol. 101 (2004).
Monster et al., "Oral Contraceptive Use and Hormone Replacement Therapy are Associated with Microalbuminuria", Arch Intern Med. 161:2000-2005 (2001).
Morrison et al., 2010, High fat diet increases hippocampal oxidative stress and cognitive impairment in aged mice: implications for decreased Nrf2 signaling, J. Neurochem. 114:1581-1589.
National Academy of Sciences, Recommended Dietary Allowances, Chromium, pp. 159-161 (1980).
Petersen, et al.: "Mild Cognitive Impairment", Arch Neurol (1999) 56:303-308.
Peterson, K R. "Pharmacodynamic Effects of Oral Contraceptive Steroids on Biochemical Markers for Arterial Thrombosis", Danish Medical Bulletin, 49:43-60 (2002).
Pi-Sunyer, et al., "Chromium" Chapter 40, Present Knowledge in Nutrition, 5th Edition, pp. 571-577 (1984).
Preuss, et al., "Comparing metabolic effects of six different commercial trivalent chromium compounds" Journal of Inorganic Biochemistry, 102:1986-1990 (2008).
Ravina, A. et al. "Clinical Use of the Trace Element Chromium (III) in the Treatment of Diabetes Mellitus" The Journal of Trace Elements in Experimental Medicine, 8:183-190 (1995).
Rangasamy et al. "Genetic ablation of Nrf2 enhances susceptibility to cigarette smoke-induced emphysema in mice", (2004) J Clin Invest 114:1248.
Reagan et al. "Regulation of GLUT-3 glucose transporter in the hippocampus of diabetic rats subjected to stress", (1999) Am. J. Physiol. Endocrinol. Metab. 276:E879-E886.
Reed et al., "A New Rat Model of Type 2 Diabetes: The Fat-fed, Streptozotocin-treated Rat" Metabolism 49(11):1390-1394 (2000).
Robins and Fasulo, "High Density Lipoproteins, But Not Other Lipoproteins, Provide a Vehicle for Sterol Transport to Bile", J. Clin. Invest. 99:380-384 (1997).
Sayre et al. "4-Hydroxynonenal-Derived Advanced Lipid Peroxidation End Products are Increased in Alzheimer's Disease", (1997) J Neurochem 68(5):2092-2097.
Sekine et al., 2006, Molecular physiology of renal organic anion transporters, Am. J Physiol Renal Physiol 290:F251-F261.
Simpson et al. "Decreased Concentrations of GLUT1 and GLUT3 Glucose Transporters in the Brains of Patients with Alzheimer's Disease", (1994) Ann. Neurol. 35:546-551.
Spady, D.K., Reverse Cholesterol Transport and Atherosclerosis Regression, 100:576-578 (1999).
Sreekanth, R. et al., "Molecular basis of chromium insulin interactions", Biochemical and Biophysical Research Communications, 369: 725-729 (2008).
Srinivasan et al., 2009, Perchlorate: health effects and tchnologies for its removal from water resources, Int. J. Environ. Res. Public Health, 6:1418-1442.
Szatmari "The Epidemiology of Attention-Deficit Hyperactivity Disorders", (1982) Child Adolesc. Psychiat. Clin. North Am. 1:361-371.
Thomas et al., 2004, The role of advanced glycation in reduced organic cation transport associated with experimental diabetes, JPET 311(2):456-466.
Uehara et al. "Chronic insulin hypoglycemia induces GLUT-3 protein in rat brain neurons", (1997) Am. J. Physiol. 272:E716-E719.
Wallin et al. "Glial Fibrillary Acidic Protein in the Cerebrospinal Fluid of Patients with Dementia", (1996) Dementia 7:267.
Wang et al., "Homozygous Disruption of Pctp Modulates Atherosclerosis in Apolipoprotein E-Deficient Mice", J Lipid Res. 47:2400-07 (2006).
Wang et al., "Involvement of Organic Cation Transporter 1 in Hepatic and Intestinal Distribution of Metformin", Journal of Pharmacology and Experimental Therapeutics, vol. 302, No. 2, pp. 510-515, 2002.
Yang et al., 2005, Differential effects of salen and manganese-salen complex (EUK-8) on the regulation of cellular cadmium uptake and toxicity, Toxicological Sciences, 85:551-559.
Yoritaka et al. "Immunohistochemical detection of 4-hydroxynonenal protein adducts in Parkinson disease", (1996) Proc. Natl. Acad. Sci. USA 93:2696-2701.
Zhang, et al., "Dynamic expression of glucose transporters 1 and 3 in the brain of diabetic rats with cerebral ischemia reperfusion", Chin Med J 2009, 122 (17); 1996-2001.
American Heart Association Dec. 6, 2000, About Cholesterol: what are healthy levels of cholesterol? (http://www.americanheart.org/cholesterol/about_level.html), 4 pp.
National Heart, Lung and Blood Institute, Mar. 11, 2007, High Blood Cholesterol—What You Need to Know (http://www.nhlbi.nih.gov/health/public/heart/chol/hbc_what.htm), 8 pp.
International Preliminary Report on Patentability dated Jan. 5, 2010 in PCT/US2008/067736.
Written Opinion of the International Search Authority dated Dec. 26, 2009 in PCT/US2008/067736.
Anonymous, 2001, New chromium formulation for easy absorption, Hutraingredients.com [online]; downloaded from URL http://www/nutraingredients.com/content/view/print/22837 on Aug. 6, 2013, 1 p.
Agency for Toxic Substances and Disease Registry, Sep. 2008, Public Health Statement: Perchlorates, 10 pp.

(56) References Cited

OTHER PUBLICATIONS

Dietary Reference Intakes (DRIs): Estimated Average Requirements, Food and Nutrition Board, Institute of Medicine, 2001, National Academies, 8 pp.
DrugBanK:Succinic Acid, Jan. 13, 2005.

* cited by examiner

MULTIPLE UNIT DOSAGE FORM HAVING A THERAPEUTIC AGENT IN COMBINATION WITH A NUTRITIONAL SUPPLEMENT

RELATED APPLICATIONS

This application is a continuation of U.S. patent application Ser. No. 14/642,243, filed on Mar. 9, 2015, which is a continuation of U.S. patent application Ser. No. 13/857,813, filed on Apr. 5, 2013, now U.S. Pat. No. 9,005,637, which is a continuation of U.S. patent application Ser. No. 12/645,124, filed Dec. 22, 2009, now U.S. Pat. No. 8,586,061, which is a continuation of International Patent Application No. PCT/US2008/067736, filed Jun. 20, 2008, which designated the United States and was published in English, which claims priority under 35 U.S.C. § 119(e) to U.S. Provisional Application Ser. No. 60/946,357, filed on Jun. 26, 2007. The content of each of these applications is hereby incorporated by reference in its entirety.

BACKGROUND OF THE INVENTION

Field of the Invention

The present invention relates to a formulation and treatment regime that provides to a patient, in a single dosage form, a combination of a therapeutic drug and a nutritional component. More particularly, the invention provides a multiple unit dosage form having a therapeutic component and a nutritional and/or vitamin component, wherein the therapeutic agent is intended for the treatment of a disease or medical condition and the nutritional component is beneficial to the patient for the same disease condition, or a related disease condition. Alternatively, the nutritional component serves to compensate for a relative or frank nutrient deficiency caused by the disease to be treated or by the therapeutic agent. Additionally, a method for the manufacture of such a formulation and the use of the formulation for the treatment of various diseases and conditions are likewise provided.

Description of the Related Art

Over the past several decades, ample evidence documents that major portions of various subgroups of individuals stratified by age, gender, socioeconomic status, and disease states, cannot meet the Recommended Dietary Allowances (RDAs) of foods containing essential compounds and elements, including specific vitamins and minerals such as calcium, potassium, iron, iodine, zinc, vitamin B12, vitamin B6, vitamin E, magnesium, folic acid, copper, selenium, and chromium. Thus, vitamin and mineral supplementation has become a recognized method of meeting acceptable medical and public health nutrition standards. Research has suggested that antioxidant micronutrients are involved in preventing molecular biological processes affecting health and disease at the subcellular and submolecular level. Specific vitamins and minerals have been shown to advance immune system integrity, moderate the aging process, and play a role in the prevention of atherosclerosis and cancer.

Vitamin and mineral preparations are commonly administered to treat specific medical conditions or as general nutritional supplements. Recent studies have elucidated the important physiological roles played by vitamins and minerals, and established a correlation between deficiencies or excesses of these nutrients and the etiologies of certain disease states in humans. See, e.g., Diplock, "Antioxidant Nutrients and Disease Prevention: An Overview," Am. J. Clin. Nutr., 53:189-193 (1991); Document Geigy Scientific Tables, 457-497 (Diem and Cemtuer eds., 7th ed., 1975).

Numerous diseases and medical conditions are caused or exacerbated by vitamin or nutritional deficiencies. Moreover, various therapeutic treatment regimes have been associated with vitamin depletion. It would therefore be desirable to provide improved therapeutics which obviate the deficiencies of known therapeutic agents while satisfying the long standing need for such therapeutic agents.

SUMMARY OF THE INVENTION

The invention disclosed herein includes a multiple unit dosage form for oral administration comprising an effective amount of a therapeutic agent, a barrier layer, and a nutritional supplement, wherein the therapeutic agent and the nutritional supplement are formulated as a single dose. In certain aspects of the invention, the barrier layer is located between the therapeutic agent and the nutritional supplement and prevents interaction between said therapeutic agent and said nutritional supplement. Advantageously, the barrier layer is comprised of a controlled-release, delayed-release, or enteric coating.

The therapeutic agent can be any of a variety of agents which include antidepressants, anti-thombotisc, anti-diabetics, anti-psychotics, and statin drugs. The nutritional supplement may be a vitamin, a mineral, an essential metal, and/or a co-enzyme. Advantageously, the dosage form is a tablet, a capsule, a gel cap, or a caplet.

In an aspect of the invention, the dosage form includes a coating on the exterior of which controls the release of the therapeutic agent and the nutritional supplement.

In another aspect of the invention, the therapeutic agent is optionally a statin drug and the nutritional supplement is co-enzyme Q10. Alternatively, the therapeutic agent may be warfarin and the nutritional supplement may be magnesium taurate. Similarly, the therapeutic agent may be sulphonylurea and the nutritionally supplement is a chromium complex. The therapeutic agent may be zidovudine and the nutritional supplement may be selenium.

When the nutritional supplement is a chromium complex, the chromium complex may be chromium polynicotinate, chromium picolinate, chromium acetate, chromium histidinate, chromium nicotinate, chromium chloride, or a chromium yeast.

In some aspects, the therapeutic agent is metformin and the nutritional supplement is a chromium complex. However, the therapeutic agent may be glipizide or olanzapine. The dosage form may additionally include a pharmaceutically acceptable carrier.

In still another aspect of the invention, the dosage form is characterized as having the therapeutic agent located at the center of the form and the nutritional supplement located at the outer portion of the form. Advantageously, he barrier layer separates the therapeutic agent from the nutritional supplement. Alternatively, the nutritional supplement may be located at the center of the form and the therapeutic agent may be located at the outer portion of the form. Again, the barrier layer separates the nutritional supplement from the therapeutic agent.

A method of restoring nutritional depletion related to a disease state is likewise provided. The method includes administering to a patient in need thereof a multiple unit dosage form for oral administration comprising an effective amount of a therapeutic agent, a barrier layer, and a nutritional supplement, wherein the therapeutic agent and the nutritional supplement are formulated as a single dose.

A method of preventing and/or attenuating depletion of a nutrient caused by the co-administration of a therapeutic agent to an individual in need thereof is also disclosed. The method includes identifying an individual presenting with nutrient depletion associated with the administration of a therapeutic agent, and administering to the individual a multiple unit dosage form for oral administration comprising an effective amount of a therapeutic agent, a barrier layer, and a nutritional supplement, wherein the therapeutic agent and the nutritional supplement are formulated as a single dose. The therapeutic agent may cause or exacerbate nutrient depletion and the nutritional supplement acts to prevent and/or attenuate the depletion.

A method of synergistically treating a disease or condition caused or exacerbated by nutrient depletion is similarly disclosed. The method includes administering to an individual in need thereof a multiple unit dosage form for oral administration comprising an effective amount of a therapeutic agent, a barrier layer, and a nutritional supplement, wherein the therapeutic agent and the nutritional supplement are formulated as a single dose.

DETAILED DESCRIPTION OF THE PREFERRED EMBODIMENT

Figure 1:
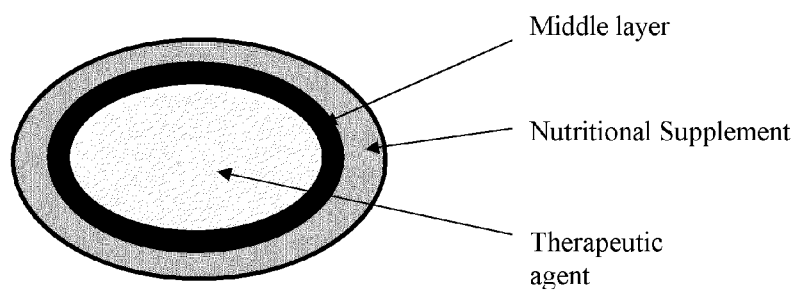
FIG. 1 is a cross-sectional view of a tablet formulation having the therapeutic agent disposed within the center of the tablet, a nutritional supplement on the outer layer of the tablet, and middle barrier layer separating the therapeutic drug from the nutritional supplement layer.

The present invention provides a novel formulation and treatment regime to a patient, wherein the course of therapy includes the use of in a single dosage form having a combination of a therapeutic drug and a nutritional supplement. More particularly, the invention offers a multiple unit dosage form having a therapeutic component and a nutritional supplement, wherein the therapeutic agent is intended for the treatment of a disease or medical condition and the nutritional supplement is beneficial to the patient for the same disease condition, or a related disease condition. As will also be described in greater detail below, the nutritional component can act to compensate for a relative or frank nutrient deficiency caused by the disease to be treated or by the therapeutic agent. Additionally, a method for the manufacture of such a formulation and the use of the formulation for the treatment of various diseases and conditions are likewise provided.

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the invention herein described.

As used herein, the phrase "therapeutic agent" is intended to have its broadest possible interpretation and refers to any therapeutically active substance that is delivered to a bodily conduit of a living being to produce a desired, usually beneficial, effect. More particularly, a therapeutic agent relates to any agent that can confer a therapeutic benefit on a patient and includes, without limitation, conventional drugs, gene therapy constructs, chemotherapeutic agents, antibiotics, macromolecules, and protein bound drugs. Exemplary therapeutic agents include analgesics, anesthetics, anxiolytics, antidepressants such as selective serotonin reuptake inhibitors like citalopram, escitalopram oxalate, fluoxetine, fluvoxamine maleate, paroxetine, sertraline, and dapoxetine, antipsychotics including clozabine, risperidone, olanzapine, quetiapine, ziprasidone, aripiprazole, paiperidone, sertindole, zotepine, amisulpride, and melperone, and olanzapine, anticonvulsants, nervous system stimulants, antiemetics, hallucinogens, mood stabilizers, bronchodilators, decongestants, anti-proliferatives, angiotensin converting enzyme inhibitors, antiarrhythmics, antianginals, antihypertensives, antihyperlipidemics including, for example, any of a number of statin drugs such as atorvastatin, cerivastatin, fluvastatin, lovastatin, mevastatin, pitavastatin, pravastatin, rosuvastatin, simvastatin, and ezetimibe with simvastatin, anticoagulants such as warfarin, acenocoumarol, phenprocoumon and phenindione, antiplatelets, beta blockers, diuretics, thrombolytics, vasodilators, antacids, antidiarrheals, H2-receptor antagonists, proton pump inhibitors, laxatives, anti-inflammatories, antirheumatics, corticosteroids, muscle relaxants, anti-histamines, antibiotics, anti-virals such as ribavirin, ganciclovir, abacavir, tenofovir, vidarabine, emtricitabine, efavirenz, darunavir, delavirdine, nevirapine, protease inhibitors, lopinavir, zalcitabine, didanosine, seliciclib, chloroquine, resveratrol, and zidovudine, vaccines, anti-protozoals, anti-fungals, antihelmintics, anti-diabetics including sulfonylureas such as tolbutamide, acetohexamide, tolazamide, chlorpropamide, glipizide, glyburide glimepiride, and gliclazide, meglitinides, biguanides such as metformin, glitazones such as rosiglitazone, pioglitazone, and troglitazone, alpha glucosidase inhibitors such as miglitol and acarbose, and DPP-4 inhibitors such as vildagliptin and sitagliptin, and chemotherapeutics which include agents such as paclitaxel, doxorubicin, and other drugs which have been known to affect tumors. Chemotherapeutics, as used herein, further includes agents which modulate other states which are related to tissues which can be permeabilized using the methods and compositions of the invention. The chemotherapeutic agent can be, for example, a steroid, an antibiotic, or another pharmaceutical composition. Examples of chemotherapeutic agents include agents such as paclitaxel, doxorubicin, vincristine, vinblastine, vindesine, vinorelbin, taxotere (DOCETAXEL), topotecan, camptothecin, irinotecan hydrochloride (CAMPTOSAR), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (ARA-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (ARA-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'(trifluorometh-yl) propionanilide, Herceptin, anti-CD20 (Rituxan), interferon alpha, interferon beta, interferon gamma, interleukin 2, interleukin 4, interleukin 12, tumor necrosis factors, and radiation. Representative compounds used in cancer therapy further include cyclophosphamide, chlorambucil, melphalan, estramustine, iphosphamide, prednimustin, busulphan, tiottepa, carmustin, lomustine, methotrexate, azathioprine, mercaptopurine, thioguanine, cytarabine, fluorouracil, vinblastine, vincristine, vindesine, etoposide, teniposide, dactinomucin, doxorubin, dunorubicine, epirubicine, bleomycin, nitomycin, cisplatin, carboplatin, procarbazine, amacrine, mitoxantron, tamoxifen, nilutamid, and aminoglutemide. Further included within the meaning of "therapeutic agents" are immuno-suppressants, hormonal contraceptions, selective estrogen receptor modulators, fertility agents, and anti-pruritics. The therapeutic agent may be formulated as microparticles or nanoparticles. Other examples of therapeutic agents include macromolecules, such as, liposomes, nanoparticles, plasmid, viral vectors, non-viral vectors, and oligonucleotides.

The phrase "nutritional supplement" is likewise intended to be afforded its broadest possible interpretation and refers to a composition that is intended to supplement the diet and bears or contains one or more of the following ingredients: a vitamin, a mineral, an herb or other botanical, an essential amino acid, an essential fatty acid, a dietary substance for use by people to supplement the diet by increasing the total dietary intake, and a concentrate, metabolite, constituent, extract, or combination of any of the above. Exemplary nutritional supplements include, without limitation, essential fatty acids such as linolenic acid and linoleic acid, and essential amino acids such as tryptophan, lysine, methionine, phenylalanine, threonine, valine, leucine, isoleucine, arginine, and histadine. Also included within the meaning of nutritional supplement are vitamins such as biotin (vitamin B7, vitamin H), choline (vitamin Bp), folate (folic acid, vitamin Bp, vitamin M), niacin (vitamin B3, vitamin P, vitamin PP), pantothenic acid (vitamin B5), riboflavin (vitamin B2, vitamin G), thiamine (vitamin B1), vitamin A (retinol), vitamin B6 (pyridoxine, pyridoxamine, or pyridoxal), vitamin B12 (cobalamin), vitamin C (ascorbic acid), vitamin E (tocopherol), co-enzyme Q10, and vitamin K (naphthoquinoids). Nutritional supplement further includes dietary minerals such as, for example, chromium (including, chromium polynicotinate, chromium picolinate, chromium acetate, chromium histidinate, chromium nicotinate, chromium chloride, and the like, or any or any pharmaceutically acceptable salts, hydrates, solvates, or mixtures thereof), bromine, cobalt, copper, fluorine, germanium, iodine, iron, magnesium, manganese, molybdenum, potassium, selenium, silicon, zinc, calcium, phosphorous, sodium, sulfur, and vanadium. The amount of nutritional supplement incorporated into the multiple unit dosage form of the present invention is quantum sufficiat to achieve the desired effect. The dosage amounts for the disclosed nutritional supplements are well-established in the arts and can be optimized for any particular indication via routine experimentation.

The term "patient" refers animals which can be treated using the compositions and methods of the invention. Examples of animals include mammals, such as mice, rabbits, rats, horses, goats, dogs, cats, pigs, cattle, sheep, and primates (e.g. chimpanzees, gorillas, and, preferably, humans).

As used herein, the phrase "over a period of time," can refer to a period of minutes, hours or days. For example, over a period of time can refer to at least 10 minutes, at least 15 minutes, at least 30 minutes, at least 60 minutes, at least 75 minutes, at least 90 minutes, at least 105 minutes, at least 120 minutes, at least 3 hours, at least 4 hours, at least 5 hours, at least 6 hours, at least 7 hours, at least 8 hours, at least 9 hours, at least 10 hours, at least 12 hours, at least 14 hours, at least 16, hours, at least 18 hours, at least 20 hours, at least 22 hours, at least one day, at least two days, at least three days, at least 4 days, at least 5 days, at least 6 days, at least a week, or any interval of time in between. In other words, the chromium from the composition can be absorbed by the individual to whom it is administered over a period of at least 10 minutes, at least 15 minutes, at least 30 minutes, at least 60 minutes, at least 75 minutes, at least 90 minutes, at least 105 minutes, at least 120 minutes, at least 3 hours, at least 4 hours, at least 5 hours, at least 6 hours, at least 7 hours, at least 8 hours, at least 9 hours, at least 10 hours, at least 12 hours, at least 14 hours, at least 16, hours, at least 18 hours, at least 20 hours, at least 22 hours, at least one day, at least two days, at least three days, at least 4 days, at least 5 days, at least 6 days, at least a week, or any interval of time in between.

As used herein, a composition that "substantially" comprises a compound means that the composition contains more than about 80% by weight, more preferably more than about 90% by weight, even more preferably more than about 95% by weight, and most preferably more than about 97% by weight of the compound. As used herein, a composition that "substantially" comprises a chromium complex refers to a composition that contains more than or equal to 7.0% of trivalent or dietary chromium. Preferably, a certificate of analysis for the compositions disclosed herein indicate that the compositions are negative for microbial growth, yeast and mold should be present in less than 300 cells/g and the toxic metals should be less than 1 ppm.

In some embodiments, the compositions disclosed herein are in the form of pharmaceutically effective salts. The phrase "pharmaceutically acceptable salt(s)," is art recognized and, as used herein includes, but is not limited to, salts of acidic or basic groups that may be present in the compositions disclosed herein. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds present in the compositions disclosed hererein that include an amino moiety also can form pharmaceutically acceptable salts with various amino acids, in addition to the acids mentioned above. Compounds present in the compositions disclosed herein that are acidic in nature are capable of forming base salts with various pharmacologically acceptable cations.

Non limiting examples of such salts include alkali metal or alkaline earth metal salts and, particularly, calcium, magnesium, sodium lithium, zinc, potassium, silicon, phosphorus and iron salts.

As used herein, the term "hydrate" means a compound or a salt thereof, that further includes a stoichiometric or non-stoichiometric amount of water bound by non-covalent intermolecular forces. The term hydrate includes solvates, which are stoichiometric or non-stoichiometric amounts of a solvent bound by non-covalent intermolecular forces. Preferred solvents are volatile, non-toxic, and/or acceptable for administration to humans in trace amount.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients; such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In one embodiment, the pharmaceutically acceptable carrier is suitable for intravenous administration. In another embodiment, the pharmaceutically acceptable carrier is suitable for locoregional injection.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted-into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

The language "pharmaceutical composition" is used interchangeably with "therapeutic agent" and includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier. The amount of therapeutic agent incorporated into the multiple unit dosage form of the present invention is quantum sufficiat to achieve the desired therapeutic effect. The dosage amounts for the disclosed therapeutic agents are well-established in the arts and can be optimized for any particular indication via routine experimentation.

Figure 2:
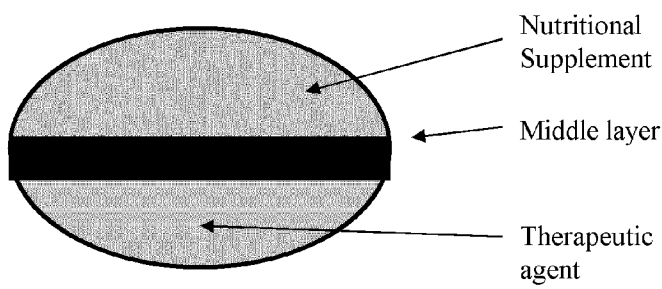
FIG. 2 is a cross sectional view of a tablet formulation having the nutritional supplement separated from the therapeutic agent by a middle barrier layer.

Turning more particularly to the disclosed invention, one object of the present invention is to provide a pharmaceutical multiple unit dosage form comprising both a therapeutic agent and a nutritional supplement, wherein the therapeutic agent and the nutritional supplement are co-formulated such that the therapeutic agent is contained in the center or core of the tablet, capsule, or gel cap and the nutritional supplement is contained on the outer portion of the tablet, capsule, or gel cap as illustrated in FIG. 1. FIG. 1 is a cross sectional view of a tablet formulation, wherein the therapeutic agent is disposed within the center of the tablet and the nutritional supplement is located on the outer layer of the tablet. Also illustrated is a middle barrier layer, which separates the therapeutic drug from the nutritional supplement layer. The middle barrier layer will be described in greater detail below. In an alternative embodiment, the therapeutic agent is formulated such that it is contained in the outer coating or outer portion of the tablet, capsule, or gel cap and the nutritional supplement is formulated at the center or core of the tablet, capsule or gel cap. In still another embodiment, the nutritional supplement and therapeutic agent are both in the center of the tablet but the two components are separated by a middle barrier layer as illustrated in FIG. 2.

As will be described in greater detail below, the formulation of the present invention includes both a nutritional supplement and a therapeutic agent for oral administration. The formulation disclosed herein can be provided as a tablet, aqueous or oil suspension, dispersible powder or granule, emulsion, hard or soft capsule, syrup, elixir, or beverage. Compositions intended for oral use can be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Tablets containing chromium complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed. The tablet, capsule, gel cap or caplet is manufactured by a standard process, for example, in the case of tablet, direct compression or a wet or dry granulation process.

In some embodiments, the compositions disclosed herein are formulated for oral delivery, for example in the form of tablets, lozenges, aqueous or oily suspensions, granules, powders, emulsions, capsules, syrups, or elixirs. Compounds and compositions described herein for oral delivery can also be formulated in foods and food mixes. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds and compositions described herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, etc. Such vehicles are preferably of pharmaceutical grade.

The nutritional supplement and therapeutic agent, pharmaceutically acceptable salts of the therapeutic agent, and pharmaceutically acceptable solvates of the therapeutic agent can be co-formulated alone but, in human therapy, will generally be administered in admixture with a suitable pharmaceutical excipient diluent or carrier selected with regard to the intended route of administration and standard pharmaceutical practice. For example, the combination therapy comprising a therapeutic agent and a nutritional supplement can be administered orally, buccally or sublingually in the form of tablets, capsules (including soft gel capsules), ovules, elixirs, solutions or suspensions, which may contain flavoring or coloring agents, for immediate-, delayed-, modified-, sustained-, or controlled-release delivery applications. Modified release dosage forms can contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release release dosage forms may contain one or a combination of release rate modifying excipients. Release rate modifying excipients can be present both within the dosage form i.e. within the matrix, and/or on the dosage form i.e. upon the surface or coating.

The tablet, capsule, gel cap, or caplet can contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc can also be included. In addition to the therapeutic and nutritional supplement components of the multiple unit dosage form, the active substances can be mixed with additional components such as binders, surfactants, fillers, disintegrating agents, alkaline additives, or other pharmaceutically acceptable ingredients, alone or in mixtures. The binders are, for example, celluloses such as hydroxypropyl methylcellulose, hydroxypropyl cellulose, and carboxymethyl-celluose sodium, polyvinyl pyrrolidone, sugars, starches, and other pharmaceutically acceptable substances with cohesive properties. In some embodiments, pharmaceutical constituents such as binders, fillers, lubricants, distintegrating agents, surfactants, and other pharmaceutically acceptable additives are likewise incorporated into the formulation.

Solid compositions of a similar type can also be employed as fillers in gelatin capsules. Preferred excipients in this regard include lactose, starch, a cellulose, milk sugar or high molecular weight polyethylene glycols. For aqueous suspensions and/or elixirs, the compounds of the invention can be combined with various sweetening or flavoring agents, coloring matter or dyes, with emulsifying and/or suspending agents and with diluents such as water, ethanol, propylene glycol and glycerin, and combinations thereof.

The compound of the invention may also be administered via fast dispersing or fast dissolving dosages forms. Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

While oral administration is preferred, the multiple unit single dosage form of the invention can also be administered parenterally, for example, intracavernosally, intravenously, intra-arterially, intraperitoneally, intrathecally, intraventricularly, intraurethrally intrasternally, intracranially, intramuscularly or subcutaneously, or it may be administered by infusion techniques. For such parenteral administration, the dosage components are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art In certain embodiments, the multiple unit dosage form includes at least one middle barrier layer comprised of pharmaceutical excipients which would separate the therapeutic agent from the nutritional supplement component. The barrier layers can be included in the formulation by art-recognized coating or layering procedures. The barrier layer is comprised of pharmaceutically acceptable compounds such as, for example, sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and anti-static agents including magnesium stearate, titanium dioxide, talc, and other additives can optionally be included in the barrier layer. Without being bound by a particular theory, it is believed that the middle barrier layer inhibits interaction of two or more components of the therapeutic agent and nutritional supplement in the single dose form and thereby can increase the efficacy of the therapeutic agent and/or nutritional supplement. In certain embodiments, the barrier layer acts as a pH-buffering zone and the layer includes at least one antacid compound selected from the group consisting of magnesium oxide, hydroxide, carbonate, aluminum or calcium hydroxide, carbonate or silicate, and composite aluminum/magnesium compounds. In a preferred embodiment, the middle barrier portion is comprised of a controlled release, delayed release, or enteric coating to control or delay the release of the inner contents of the multiple unit dosage form. The middle layer advantageously improves the rate of absorption of the therapeutic agent and/or nutritional supplement. In one embodiment, the middle barrier layer increases the efficacy of the therapeutic agent and/or nutritional supplement.

In another embodiment, the multiple unit dosage form further includes an outer coating. The outer coating serves to provide an immediate release, controlled-release, delayed-release, or enteric-coating to control or delay the release of the therapeutic agent and nutritional supplement component. The outer coating layer (or layers) can be applied by coating or layering procedures which are well-established in the relevant arts. The outer coating layer is at least one of a pharmaceutically acceptable compound selected from the group consisting of sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and combinations thereof. Additives including plasticizers, colorants, pigments, fillers, anti-tacking and anti-static agents can optionally be included in the outer coating.

In preferred embodiments, the outer coating regulates release of the therapeutic and/or nutritional supplement component from the tablet, capsule, gel cap, or caplet. Controlled-release, delayed-release, and/or enteric-coating technology is well-established in the pharmaceutical and formulation arts. It is of great advantage to both the patient and the physician that medication be formulated so that it may be administered in a minimum number of daily doses from which the drug is uniformly released over a desired extended period of time. This effect is accomplished using sustained or slow release compositions. Sustained or slow release compositions containing pharmaceutical medicaments or other active ingredients are designed to contain higher concentrations of the medicament and are prepared in such a manner as to affect sustained or slow release into the gastrointestinal digestive tract of humans or animals over an extended period of time.

Well absorbed oral sustained or slow release therapeutic drug dosage forms have inherent advantages over conventional, immediate release dosage forms. The advantages include less frequent dosing of a medicament and resultant patient regime compliance, a more sustained drug blood level response, therapeutic action with less ingested drug and the mitigation of side effects. By providing a slow and steady release of the medicament over time, absorbed drug concentration spikes are mitigated or eliminated by affecting a smoother and more sustained blood level response.

Various hydrophilic and hydrophobic materials, including polymers, can be utilized in preparing sustained release formulations. These formulations are prepared by various methods well-established in the tableting arts, such as solvent evaporation, heat melting, direct compression and wet granulation. In some embodiments, waxes and lipids are used as coating material to retard the release of drugs. The common methods of manufacturing sustained release medicaments in oral dosage forms using waxes as the controlled release material admixed with the medicament are (a) melting the drug and wax together, then cooling and milling the melt, and finally tableting after mixing with excipient; (b) using wet granulation techniques, employing an organic solvent as a granulating medium; (c) mixing the drug and waxes in a high shear mixture and using the heat produced during the processing to achieve a homogenous mixture; and (d) using heat radiation to effect melting of the wax in the presence of the drug.

In one embodiment of the invention, controlled release coatings are prepared by forming a matrix by entrapping the therapeutic agent and/or nutritional supplement in excipients. Diffusion and/or erosion operate to release the active therapeutic and/or nutritional supplement substance depending on the properties of the active agent and the polymer incorporated in the formulation. One particular attempt at controlled release is detailed in European Patent publication 0 593 309 A2 to Columbo, hereby incorporated by reference in its entirety. The publication shows a three-layer system consisting of two external swelling layers separated by an interposed soluble layer, and a two-layer system consisting of a swellable layer adjacent a soluble and/or erodible layer. The swellable layer(s) consist of methyl cellulose, carboxymethylcellulose sodium, crosslinked carboxymethylcellulose sodium, crosslinked hydroxypropylcellulose, hydroxypropylmethylcellulose, carboxymethyl starch, polymethacrylate, polyvinylpyrrolidone, polyvinyl alcohols, polyethylene glycols, or potassium methacrylate-divinyl benzene copolymer and mixtures thereof.

The soluble and/or erodible layer includes hydroxyethylcellulose, carboxymethylcellulose, alginates, albumin, soluble starch and/or gelatin, mixed with at least one soluble excipient such as saccharide and polyalcohol. In one embodiment, the swellable layer(s) contain an active therapeutic agent. As the swellable layers swell and the erodible layer erodes, the therapeutic agent is released from the swellable layers. In another embodiment, the swellable layer(s) contain a nutritional supplement. In yet another embodiment, the swellable layer(s) contain both the active therapeutic agent and the nutritional supplement.

In certain embodiments, the multiple unit dosage form of the present invention includes an enteric coating layer. The enteric coating layer(s) are applied using a suitable coating technique. The enteric coating layer material can be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). The enteric coating layers contain pharmaceutically acceptable plasticizers to obtain the desired mechanical properties such as flexibility and hardness of the enteric coating layers. Such plasticizers are, for instance, but not restricted to, triacetin, citric acid esters, phthalic acid esters, dibutyl sebacate, cetyl alcohol, polyethylene glycols, polysorbates or other plasticizers. The amount of plasticizer is optimized for each enteric coating layer formula in relation to selected enteric coating layer polymer(s), selected plasticizer(s) and the applied amount of the polymer(s), in such a way that the mechanical properties such as flexibility and hardness of the enteric coating layers, are adjusted so that the acid resistance of the formulation does not decrease significantly during the compression of the components into tablets, for example. The amount of plasticizer is usually above 10% by weight of the enteric coating layer polymer(s), preferably 15-50%, and more preferably 20-50%. Additives such as dispersants, colorants, pigments, polymers, anti-tacking and anti-foaming agents can likewise be included into the enteric coating layer(s). In some embodiments, other compounds can be added to increase film thickness and to decrease diffusion.

The present invention further includes a single dose form having a therapeutic agent and a nutritional supplement in a capsule. Capsule formulation is well-established in the pharmacological arts. See, e.g., U.S. Pat. No. 3,965,256 to Leslie, the entire contents of which are hereby incorporated by reference. Slow release capsules are prepared by filling the appropriate quantity of the above described tablet granulation mixture into gelatin capsules of suitable size and shape, with slight modification such as, for example, eliminating the tablet lubricant or the tablet binder. A slow release capsule may contain the mixture of the appropriate quantity of the combination of higher aliphatic alcohol and hydrated hydroxy-alkyl cellulose together with the active ingredients (a therapeutic agent and a nutritional supplement) and diluent. The diluent serves to achieve the appropriate concentration of the slow release composition within the unit dosage form. As for the slow release tablet preparations, the time span for the release of the active ingredient in the capsule formulation will depend upon the concentration of the slow release composition within the total weight of the capsule formulation.

Formulations for oral use can be presented as hard gelatin capsules wherein the active ingredients (i.e., the therapeutic agent and the nutritional supplement) are mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the chromium complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Figure 3:
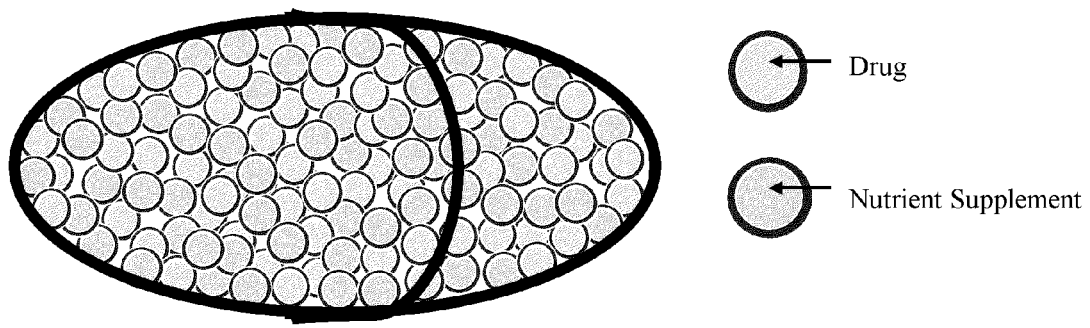
FIG. 3 is a perspective view of a capsule, wherein the capsule is comprised of therapeutic agent beadlets and nutritional supplement beadlets.

When the multiple unit single dose form of the present invention is formulated as a capsule, the therapeutic agent and nutritional supplement are, in certain embodiments, formulated in microcapsules or beadlets, wherein the therapeutic agent and the nutritional supplement are contained in separate microcapsules or beadlets as illustrated in FIG. 3. Preferably, the microcapsules or beadlets are protected by an outer coating as described above with reference to tablet formulations.

Figure 4:
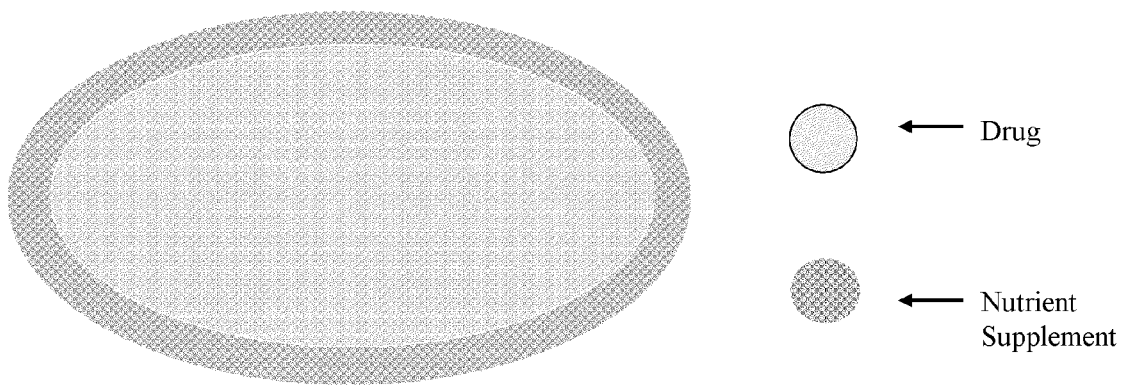
FIG. 4 is a cross-sectional view of a gelcap having a therapeutic agent incorporated within the liquid component of the gelcap and a nutritional supplement incorporated within the gelatin exterior of the gelcap.

In another embodiment, the multiple unit single dose form is formulated as a softgel capsule, wherein the therapeutic agent is located within the center of the capsule in liquid or semi-liquid form and the nutritional supplement is integrated into the outer layer of the capsule as illustrated in FIG. 4. In an alternate embodiment, the softgel capsule includes the nutritional supplement within the center of the capsule in liquid or semi-liquid form and the therapeutic agent is incorporated within the outer layer of the capsule. Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

It will be appreciated by the skilled artisan that the amount of therapeutic agent in combination with nutritional supplement that can be combined with the carrier material to produce a single dosage form will vary depending upon the host treated and the particular mode of administration.

When administered to a mammal, e.g., to an animal for veterinary use or for improvement of livestock, or to a human for therapeutic use, the compositions disclosed herein are administered in isolated form or as the isolated form in a therapeutic composition. As used herein, "isolated" means that the compositions disclosed herein are separated from other components of either (a) a natural source, such as a plant or cell or food, preferably bacterial culture, or (b) a synthetic organic chemical reaction mixture. Preferably, via conventional techniques, the compositions disclosed herein are purified. As used herein, "purified" means that when isolated, the isolate contains at least 95%, preferably at least 98% of the composition.

Compositions and methods for restoring a nutrient depletion related to a particular disease state are likewise disclosed. The present invention is based, in part, on the surprising discovery that a composition comprising both a nutritional supplement and a therapeutic agent can be administered as a single unit dose form, wherein the therapeutic agent treats a disease or medical condition and the nutritional supplement component addresses the nutritional deficiencies associated with that same disease or condition. For example, a dietary magnesium (Mg) deficiency is often associated with cardiovascular disease and/or stroke. Mg deficiency can cause cardiovascular lesions leading to disease at all stages of life. Otherwise normal, Mg deficient diets cause arterial and myocardial lesions in all animals, and diets that are atherogenic, thrombogenic and cardiovasopathic, as well as Mg-deficient, intensify the cardiovascular lesions, whereas Mg supplementation prevents them. Diuretics and digitalis can intensify an underlying Mg deficiency, leading to cardiac arrhythmias that are refractory unless Mg is added to the regimen. A composition comprising an anti-thrombotic such as warfarin or Plavix® and magnesium taurate, for example, can address both the underlying disease as well as the nutrient depletion related to the cardiovascular disease state. Similarly, in HIV/AIDS patients, a depletion of selenium has been observed and can result in cardiomyopathy. The administration of a composition comprising both selenium and an HIV/AIDS drug, e.g. zidovudine, would supplement the dearth of nutritional selenium and treat the symptoms of the underlying viral infection. In certain embodiments, the compositions disclosed herein are provided to a subject, such as a mammal, as a preventative measure against such diseases. As used herein, "prevention" or "preventing" refers to a reduction of the risk of acquiring a given disease or disorder alone or in combination with other clinical condition. A tablet comprising selenium and zidovudine, for example, can not only treat selenium depletion associated with HIV/AIDS but also prevent the depletion of selenium in an individual identified with the disease but not yet exhibiting symptoms of selenium depletion.

Compositions and methods for addressing nutrient depletion caused by a therapeutic drug regime are likewise provided. Various therapeutic interventions have been shown to deplete nutrients in individuals being treated with certain pharmaceutical drugs. For example, statin drugs, or HMG-CoA reductase inhibitors, are a class of drugs used to lower cholesterol. Statins work by inhibiting the enzyme HMG-CoA reductase, the enzyme that determines the rate of cholesterol formation. Some research suggests that statin drugs may interfere with the body's production of co-enzyme Q10 (Co q10), a substance produced naturally in the body and found in every cell. Co q10 has a key role in the mitochondria, the part of a cell that produces energy. Statins have been found to decrease Co q10 production as a side effect of their action. A Columbia University study in New York found that 30 days of statin therapy (80 mg/day) decreased Co q10 levels by half. Another study by researchers at Kanazawa University in Japan found that smaller doses of statin drugs can reduce Co q10. After 8 weeks of 10 mg a day statin therapy, Co q10 levels decreased by 40 percent. Some researchers have therefore suggested that this side effect may counteract any benefits of taking statins. By providing a multiple unit single dosage form comprising a statin drug such as lovastatin or simvastatin as the therapeutic component and Co q10 as the nutritional supplement component, the negative impact of statin drugs is greatly attenuated. The administration of a multiple unit single dosage form having Co q10 as the nutritional supplement component prevents the depletion of Co q10 and/or attenuates the depletion of Co q10 caused by statin drug therapy.

In yet another embodiment, compositions and methods for providing a combination therapy with a single, multiple unit tablet, capsule, caplet, or gel cap is disclosed. The nutritional supplement and therapeutic drug act at least additively and more preferably, synergistically, to treat a disease or medical condition. One example of such a combination therapy includes a tablet comprising a conventional anti-diabetic drug such as metformin or glipizide formulated in the center of a tablet, a controlled release middle barrier layer which would act to delay the release of the therapeutic agent, and chromium on the outer coating of the tablet. Preferably, an outer coating to facilitate transport of chromium is included on the outermost (relative to the center) portion of the tablet.

Dietary supplementation of chromium to normal individuals has been reported to lead to improvements in glucose tolerance, serum lipid concentrations, including high-density lipoprotein cholesterol, insulin and insulin binding. Anderson, 1986 *Clin. Psychol. Biochem.* 4:31-41. Supplemental chromium in the trivalent form, e.g. chromic chloride, is associated with improvements of risk factors associated with adult-onset (Type 2) diabetes and cardiovascular disease. Chromium is essential for optimal insulin activity in all known insulin-dependent systems. Boyle et al., 1977 *Southern Med. J.* 70:1449-1453. Insufficient dietary chromium has been linked to both maturity-onset diabetes and to cardiovascular disease.

Chromium functions as a cofactor for insulin. It binds to the insulin receptor and potentiates many, and perhaps all, of its functions. Boyle et al., supra. These functions include, but are not limited to, the regulation of carbohydrate and lipid metabolism. Present Knowledge in Nutrition, supra, at p. 573-577. The introduction of inorganic chromium compounds per se into individuals is not particularly beneficial. Chromium must be converted endogenously into an organic complex or must be consumed as a biologically active molecule. Only about 0.5% of ingested inorganic chromium, however, is assimilated into the body. Only 1-2% of most organic chromium compounds are assimilated into the body. Recommended Daily Allowances, Ninth Revised Edition, The National Academy of Sciences, page 160, 1980.

U.S. Pat. No. Re. 33,988 discloses that when selected essential metals, including chromium, are administered to mammals as exogenously synthesized coordination complexes of picolinic acid, they are directly available for absorption without competition from other metals. U.S. Pat. No. Re. 33,988 describes a composition and method for selectively supplementing the essential metals in the human diet and for facilitating absorption of these metals by intestinal cells. These complexes are safe, inexpensive, biocompatible, and easy to produce. These exogenously synthesized essential metal coordination complexes of picolinic acid (pyridine-2-carboxylic acid) have the following structural formula:

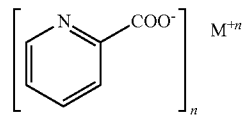

wherein M represents the metallic cation and n is equal to the cation's valence. For example, when M is Cr and n=3, then the compound is chromic tripicolinate. Other chromium picolinates disclosed include chromic monopicolinate and chromic dipicolinate.

The U.S. Recommended Daily Intake (RDI) of chromium is 120 µg. U.S. Pat. No. 5,087,623, the entire contents of which are hereby expressly incorporated herein by reference, describes the administration of chromic tripicolinate for the treatment of adult-onset diabetes in doses ranging from 50 to 500 µg. U.S. Pat. No. 6,329,361, the entire contents of which are hereby expressly incorporated herein by reference, discloses the use of high doses of chromic tripicolinate (providing 1,000-10,000 µg chromium/day) for reducing hyperglycemia and stabilizing the level of serum glucose in humans with Type 2 diabetes. U.S. Pat. Nos. 5,789,401 and 5,929,066, the entire contents of which are hereby expressly incorporated by reference, disclose a chromic tripicolinate-biotin composition and its use in lowering blood glucose levels in humans with Type 2 diabetes.

U.S. Pat. Nos. 5,087,623; 5,087,624; and 5,175,156, the entire contents of which are hereby expressly incorporated herein by reference, disclose the use of chromium tripicolinate for supplementing dietary chromium, reducing hyperglycemia and stabilizing serum glucose, increasing lean body mass and reducing body fat, and controlling serum lipid levels, including the lowering of undesirably high serum LDL-cholesterol levels and the raising of serum High Density Lipid (HDL)-cholesterol levels. U.S. patent application Ser. Nos. 10/090,038 and 11/136,794, the entire contents of which are hereby expressly incorporated by reference in their entireties, disclose the use of high doses of chromium complexes (providing between 1,000 and 10,000 µg/day) and biotin for treating dyslipidemia, and increasing serum HDL levels.

U.S. Pat. Nos. 4,954,492 and 5,194,615, the entire contents of which are hereby expressly incorporated by reference, describe a related complex, chromic nicotinate, which is also used for supplementing dietary chromium and lowering serum lipid levels. Picolinic acid and nicotinic acid are position isomers having the following structures:

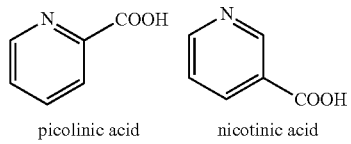 [SMILES: O=C(O)c1ccccn1 ; O=C(O)c1cccnc1]

picolinic acid    nicotinic acid

Nicotinic acid and picolinic acid form coordination complexes with monovalent, divalent and trivalent metal ions and facilitate the absorption of these metals by transporting them across intestinal cells and into the bloodstream and in some embodiments, nicotinic acid and/or picolinic acid are incorporated into the outer coating of the tablet formulation to augment the efficacy of the combination therapy. In some embodiments, uncomplexed chelating agents are advantageously included in the single dosage either with the nutritional supplement layer or as a separate coating layer to facilitate absorption of other ingested chromium as well as other metals including, but not limited to, copper, iron, magnesium, manganese, and zinc. Suitable chelating agents include histidine, any essential amino D or L amino acids, tri amino acid formulae including but not limited to, triphenylalanine, tri histidine, tri arginine, picolinic acid, nicotinic acid, or both picolinic acid and nicotinic acid. Chelating agents such as histidine, picolinic acid and nicotinic acid are available from many commercial sources, including Sigma-Aldrich (St. Louis, Mo.) (picolinic acid; catalog No. P5503; nicotinic acid; catalog No. PN4126). Preferably, the ratio of the chromium complex to the chelating agent from about 10:1 to about 1:10 (w/w), more preferably from about 5:1 to about 1:5 (w/w). Alternatively, the molar ratio of chromium complex to the uncomplexed chelating agent is preferably 1:1, and may be from about 5:1 to about 1:10. More than one chelating agent, e.g, both nicotinic and picolinic acid can be included in the compositions disclosed herein, or administered to subject in the methods described herein.

The amount of a compound of the invention that will be effective in the treatment of a particular disorder or condition disclosed herein will depend on the nature of the disorder or condition, and can be determined by standard clinical techniques. As used herein, the term "treatment" or "treating" refers to an amelioration of a disease or disorder, or at least one discernible symptom thereof. The term "treatment" or "treating" refers to inhibiting the progression of a disease or disorder, either physically, e.g., stabilization of a discernible symptom, or physiologically, e.g., stabilization of a physical parameter, or both.

In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each circumstance. Suitable dosage ranges of metformin are well-established. Suitable dosage ranges for oral administration are generally about 0.001 milligram to 5000 milligrams of a total chromium complex per kilogram body weight. In preferred embodiments, the oral dose is 0.01 milligram total chromium complex to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. The dosage amounts described herein refer to total amounts administered; that is, if more than one chromium complex or more than one composition disclosed herein is administered, the preferred dosages correspond to the total amount of the compositions disclosed herein administered. Oral compositions preferably contain 10% to 95% active ingredient.

In accordance with the methods disclosed herein, the amount of chromium provided by the compositions that comprise chromium complexes disclosed herein can be at least 50 μs per day, for example at least 60 μg, at least 70 μg, at least 80 μg, at least 90 μg, at least 100 μg, at least 125 μg, at least 150 μg, at least 200 μg, at least 250 μg, at least 300 μg, at least 350 μg, at least 400 μg, at least 450 μg, at least 500 μg, at least 550 μg, at least 600 μg, at least 650 μg, at least 700 μg, at least 750 μg, at least 800 μg, at least 850 μg, at least 900 μg, at least 950 μg, at least 1,000 μg, at least 1500 μg, at least 2,000 μg, at least 2500 μg, at least 3000 μg, at least 3500 μg, at least 4000 μg, at least 4500 μg or at least 5000 μg chromium complex/day. As discussed above, chromium complexes may be trivalent complexes, such as chromium picolinate, chromic tripicolinate, chromium nicotinate, chromic polynicotinate, chromium chloride, chromium histidinate, chromium yeast, or any other chromium complex, whether now known or to be developed in the future.

By way of example, the level of chromium used for supplementation in order to inhibit the onset of insulin resistance is at least about 50 μg/day. Chromium picolinate and chromium chloride have been administered to rats at levels several thousand times the upper limit of the estimated safe and adequate daily dietary intake (ESADDI) for chromium for humans (based on body weight) without toxic effects. R. Anderson et al., Lack of Toxicity of Chromium Chloride and Picolinate, 16 J. Am. Coll. Nutr. 273-279 (1997). While the level of chromium used for supplementation may be within several thousand times the upper limit of the ESADDI, preferably, the amount of chromium is between about 50 and 2,000 μg/day. More preferably, the amount of chromium is between about 300 and 1,000 μg/day. Most preferably, the amount of chromium is between about 400 and 1,000 μg/day. In a particularly preferred embodiment, the amount of chromium is between about 600 and 1,000 μg/day. These doses are based on a 70 kg adult human, and that the dose can be applied on a per-kilogram basis to humans or animals of different weights.

In some embodiments, the amount of fast-acting chromium complex and the amount of slow acting chromium complex in a composition provide a greater than additive effect in lowering serum glucose levels than either complex alone. In some embodiments, the amount of fast-acting chromium complex and the amount of slow-acting chromium complex in a composition provide a synergistic or greater than additive effect in improving insulin sensitivity. In some embodiments, the amount of fast-acting chromium complex and the amount of slow-acting chromium complex in a composition provide a greater than additive effect in treating dyslipidemia. In some embodiments, the amount of fast-acting chromium complex and the amount of slow-acting chromium complex in a composition provide a greater than additive effect in increasing lean muscle mass.

In some embodiments, the compositions disclosed herein are provided in an amount effective for the prevention of insulin resistance. As used herein, the term "insulin resistance (IR)" refers to a physiologically abnormal state in which cells do not respond appropriately to insulin, such that glucose in the blood cannot efficiently enter cells and, therefore, leads to hyperglycemia. Insulin resistance is believed to affect one in three adult Americans which amounts to approximately 99.3 million Americans with some degree of insulin resistance. The cardiovascular and metabolic disturbances associated with IR can individually and interdependently lead to a substantial increase in cardiovascular disease (CVD) morbidity and mortality, making the cardiometabolic syndrome an established and strong risk factor for premature and severe CVD and stroke. For example, in some embodiments, a subject is provided a single multiple unit dosage composition comprising metformin in combination with a sufficient amount of a chromium complex to inhibit or reduce the risk of the onset of insulin resistance. The assessment of the affects of the compositions on insulin resistance can readily be determined using routine techniques known to those skilled in the art, and described, for example, in U.S. patent application Ser. No. 10/090,038. The chromium complex may include chromium picolinate, chromic tripicolinate, chromium nicotinate, chromic polynicotinate, chromium chloride, chromium histidinate, chromium yeast, or other chromium complex, whether now known or to be developed in the future. Effective doses of metformin are art-established. Effective doses of chromium complex may be extrapolated from dose-response curves derived from in vitro or animal model test systems. Such animal models and systems are well known in the art. Preferably, the sufficient amount of chromium provided by the chromium complex and contained in the composition is between about 50 µg and 2000 µg.

Therapeutic Uses of Dosage Form Comprising a Therapeutic and a Nutritional Supplement In certain embodiments, the compounds and compositions disclosed herein can be used as combination therapy with at least one therapeutic agent and at least one nutritional supplement. The nutritional supplement and the therapeutic agent can act additively or, more preferably, synergistically. In one embodiment, a composition comprising, consisting essentially of, or consisting of an anti-diabetic agent with a chromium complex is administered to an individual with diabetic nephropathy, diabetic retinopathy, a disorder of glucose metabolism, dyslipidemia, dyslipoproteinemia, insulin resistance, lipid elimination in bile, modulating C reactive protein, obesity, and/or metabolic syndrome disorders (e.g., Syndrome X) to improve glucose tolerance and/or later lipid metabolism. As used herein, the term "improving glucose tolerance" indicates an observable (measurable) change in at least one aspect of glucose metabolism, including but not limited to total blood glucose content, blood insulin, the blood insulin to blood glucose ratio, glycosylated hemoglobin, HOMAIR, beta cell function, composite of insulin sensitivity index, hyperglycemia, hyperglycemia, hypoglycemia, hormones, enhancing enzyme activities, improving hormonal balance caused due to insulin resistance, abnormal glucose metabolism, lipodystrophy, reducing brain insulin resistance, insulin sensitivity, and oxygen consumption. Abnormal glucose metabolism in conditions like polycystic ovary syndrome, HIV, HIV lipodystrophy, Alzheimer's disease, mental health disorders, lipodystrophy, hormonal imbalance conditions, hypertension, obesity and cardiovascular disease and cardiometabolic syndrome. As used herein, the term "altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids, esters of fatty acids, isomers, isoforms and ratios and improving ratios for reducing chronic disease risk but not limited to diabetes, obesity, hypertension, coronary heart disease and cardiovascular disease.

In another embodiment, a composition comprising, consisting essentially of, or consisting of an anti-inflammatory and a chromium complex are administered to treat a thrombotic disorder, inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis or other soft tissue rheumatism. Treatment or prevention of inflammation is similarly contemplated and encompasses, but is not limited to, chronic inflammatory disorders of the joints including arthritis, e.g., rheumatoid arthritis and osteoarthritis; respiratory distress syndrome, inflammatory bowel diseases such as ileitis, ulcerative colitis and Crohn's disease; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy.

"Insulin resistance" refers to a condition characterized by decreased insulin function and hyperinsulinemia, caused or exacerbated by drugs and disease conditions such to obesity, diabetes, CVD in a human or other animal. Examples of drugs which induce insulin resistance include, without limitation, statin drugs such as simvastatin, cerivastatin, pravastatin, atorvastatin, fluvastatin, and lovastatin; non-steroidal anti-inflammatory drugs such as cimicifuga, choline salicylate-magnesium salicylate, diclofenac sodium, diclofenac potassium, diflunisal, etodolac, fenoprofen calcium, floctafenine, flurbiprofen, ibuprofen, indomethacin, ketoprofen, ketorolac tromethamine, magnesium salicylate, mefenamic acid, nabumetone, naproxen, naproxen sodium, oxyphenbutazone, phenylbutazone, piroxicam, salsalate, sodium salicylate, sulindac, tenoxicam, taiprofenic acid, and tolmetin sodium; steroids such as hydrocortisone, dexamethasone, and methylprednisolone; contraceptives including oral contraceptives such as estrogen, progesterone and progestin as well as implantable contraceptives such as levonorgestrel, etonogestrel, nomegestrol acetate, and nestorone; hormone replacement therapy (HRT) drugs including conjugated equine estrogens, esterified estrogens, estradiol, estrone, synthetic conjugated estrogens, estropipate, estropipate, ethinyl estradiol, norethindrone, medroxyprogesterone acetate, progestin, natural progesterone, tamoxifen, testosterone, and raloxifene; beta blocker drugs including acebutolol, atenolol, betaxolol, bucinodol, carteolol, labetalol, metoprolol, nadolol, penbutolol, pindolol, propanolol, and timolol; and diuretics. Three primary types of diuretics exist which include thiazides, loop diuretics, and potassium sparing agents. As used herein, the term "diuretic" or "diuretics" includes, without limitation, hydrochlorothiazide, chlorthalidone, chlorothiazide, indapamide, metolazone, amiloride, spironolactone, triamterene, furosemide, bumetanide, ethacrynic acid, and torsemide. Certain immunosuppressive drugs such as prednisolone, cyclosporin A, and tacromlimus and potassium channel modulators such as nicorandil are also included in the definition of drugs which induce insulin resistance, such as, for example, antidepressants. The above list is provided for example purposes only and it is understood that the definition of "drug which induces insulin resistance" includes those drugs which induce insulin resistance that are not specifically listed above, as well as those drugs which are found to induce insulin resistance, whether in existence today or developed in the future. The co-formulation of a drug which induces insulin resistance with a nutritional supplement which treats or prevents insulin resistance such as chromium as a single tablet or capsule reduces the likelihood of induction of insulin resistance. By not developing insulin resistance in the first place, the patient is not exposed to the associated diseases and risks.

Insulin resistance is a key pathogenic parameter of Type 2 diabetes, and clinical interventions that improve insulin sensitivity are considered cornerstones in the management of the disease. In addition, the relationship of insulin resistance to cardiovascular disease and its associated risk factors has been well established over the past few years. Therefore, in a preferred embodiment, methods and compositions for thwarting the development of insulin resistance are provided comprising the administration of a multiple unit dosage form having a hypoglycemic drug such as metformin, which inhibits insulin resistance from developing with a chromium complex. Combinations of pharmacologic agents (such as sulfonylureas/metformin, sulfonylureas/glitazones, and metformin/glitazones) are highly effective pharmacologic interventions that appear to lower both glucose and insulin levels. Further, there is evidence that triple drug therapy (e.g. sulfonylureas/metformin/glitazones) can lower clinical glycemia in addition to lowering insulin levels. Hence, in some embodiments, compositions comprising a chromium complex with metformin, sulfonylureas, and glitazones or combinations thereof are administered to a subject taking drugs which induce insulin resistance to inhibit the onset of such insulin resistance.

The disclosure represents the present technology in that the subject has a chance of developing insulin resistance or diabetes or associated conditions but not limited to cardiovascular disease, obesity, diabetes, combination one or two disease conditions based on ATPIII guidelines and or due to mental health conditions such as depression, schizophrenia, Alzheimers disease and other conditions such HIV and HIV lipodystrophy and polycystic ovary syndrome. The insulin resistance might be due to family history, body weight, diet and drugs. The patient also does not need to take additional, and sometimes costly, medications to treat the insulin resistance and associated diseases.

Treatment of Cardiovascular Diseases

The present invention provides compositions and methods for the treatment or prevention of a cardiovascular disease, comprising administering to a patient a therapeutically effective amount of a composition comprising, consisting essentially of, or consisting of a conventional cardiovascular therapeutic and a nutritional supplement with a pharmaceutically acceptable vehicle. As used herein, the term "cardiovascular diseases" refers to diseases of the heart and circulatory system. These diseases are often associated with dyslipoproteinemias and/or dyslipidemias and/or familial hyperlipoproteinemias, hyper cholesterolemia and hyper lipidemia. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarction; cerebral infarction and restenosis. Also included are related pathologies, such as, for example, hypertrophy, hypertension, congestive heart failure, myocardial ischemia, ischemia reperfusion injuries in an organ, arrhythmia, and myocardial infarction. One embodiment is directed to a method of treating cardiovascular disease in a mammal by concurrently administering to the mammal a therapeutically effective amount of a combination of warfarin as the therapeutic agent component and magnesium taurate as the nutritional supplement component.

Treatment of Dyslipidemias

Also provided are compositions and methods for the treatment or prevention of a dyslipidemia comprising administering to a patient a therapeutically effective amount of a multiple unit dosage form having a statin drug and co-q10 and a pharmaceutically acceptable vehicle.

As used herein, the term "dyslipidemias" refers to disorders that lead to or are manifested by aberrant levels of circulating lipids. To the extent that levels of lipids in the blood are too high, the compositions described herein are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org/cholesterol/about_level.html and http://www.nhlbi.nih.gov/health/public/heart/chol/hbc_what.html, respectively). At the present time, the recommended level of HDL cholesterol in the blood is above 35 mg/dL; the recommended level of LDL cholesterol in the blood is below 70 mg/dL if they have multiple risk factors; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. .beta.-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a tablet, capsule, or other suitable vehicle for oral administration comprising an effective dose of a statin drug with an effective dose of co-Q10.

Treatment of Glucose Metabolism Disorders

Also provided are compositions and methods for the treatment or prevention of a glucose metabolism disorder, comprising providing to a subject with or at risk of developing a glucose metabolism disorder a therapeutically effective amount of a fast-acting chromium complex and slow-acting chromium complex and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions described herein are administered to a patient to restore normal levels. Conversely, to the extent that indicia of glucose metabolism are too low, the compositions described herein are administered to a patient to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to type 2 diabetes, type 1 diabetes, gestational diabetes mellitus (GDM), and maturity onset diabetes of the young (MODY); pancreatitis; hypertension; polycystic ovarian disease; HIV lipodystrophy, hormonal imbalance, hypercotisol levers, endothelial dysfunction, Alzheimers disease, aging and high levels of blood insulin and/or glucose.

Further provided are compositions and methods for altering glucose metabolism in a patient, for example to increase insulin sensitivity and/or oxygen consumption of a patient, comprising administering to the mammal an oral formulation comprising a therapeutic drug effective in altering glucose metabolism and a chromium complex in an amount effective to alter glucose metabolism.

Treatment of Cancer

Provided herein are compositions and methods for the treatment or prevention of cancer and related conditions. Cancer, including, but not limited to, a tumor, metastasis, or any disease or disorder characterized by uncontrolled cell growth, can be treated or prevented by combination therapy with a chemotherapeutic and nutritional supplementation as described herein. Cachexia, a condition related to cancer, is a systemic disease of which the cardinal symptoms are progressive weight loss, anemia, edema, loss of appetite and so forth. It may occur as a side-effect of certain chronic diseases, such as malignant tumors, tuberculosis, diabetes, blood diseases, endocrine diseases, infections and acquired immune deficiency syndrome. When cachexia occurs as a result of the presence of a malignant tumor, even if the administration of antitumor drugs to the patient with malignant tumor is effective and antitumor effects are experienced, there is normally no improvement in the cachexia because of adverse effects such as the myelotoxicity which may be caused by the antitumor drug. Since the strength of a patient is greatly depleted as cachexia progresses, it may become impossible to continue treatment using antitumor drugs (which generally exhibit a high level of toxicity), and this thereby becomes an obstacle to the treatment of the malignant tumor.

Nutritional supplements are often given in order to treat the symptoms of cachexia. This, however, often enhances the progress of the malignant tumor, and may shorten the survival time of the patient. The present invention provides a composition and method for treating cancer and related conditions. The method includes administering to a patient a therapeutically effective amount of a composition comprising a chemotherapeutic agent as the therapeutic agent, a nutritional supplement, and a pharmaceutically acceptable vehicle. Types of cancer that can be treated using combination chromium supplementation include, but are not limited to solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas cystadenocarcinoma, medullary carcinoma, bronchogenic carcinoma, renal cell carcinoma, hepatoma bile duct carcinoma choriocarcinoma seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme astrocytoma medulloblastoma, craniopharyngioma, ependymoma, pinealoma, hemangioblastoma acoustic neuroma, oligodendroglioma, meningioma, skin cancer, melanoma, neuroblastoma, retinoblastoma, Blood-borne cancers, including but not limited to: acute lymphoblastic B-cell leukemia, acute lymphoblastic T-cell leukemia, acute myeloblastic leukemia, "AML," acute promyelocytic leukemia "APL," acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, "CML," chronic lymphocytic leukemia, "CLL," hairy cell leukemia, multiple myeloma Acute and chronic leukemias, Lymphoblastic myelogenous leukemias, lymphocytic myelocytic leukemias, Lymphomas: such as Hodgkin's disease, non-Hodgkin's Lymphoma, Multiple myeloma, Waldenstrom's macroglobulinemia, Heavy chain disease, and Polycythemia vera.

The chemotherapeutic agent can be at least one of paclitaxel, doxorubicin, and/or other drugs which have been known to affect tumors. Chemotherapeutics, as used herein, further includes agents which modulate other states which are related to tissues which can be permeabilized using the methods and compositions of the invention. The chemotherapeutic agent can be, for example, a steroid, an antibiotic, or another pharmaceutical composition. Examples of chemotherapeutic agents include agents such as paclitaxel, doxorubicin, vincristine, vinblastine, vindesine, vinorelbin, taxotere (DOCETAXEL), topotecan, camptothecin, irinotecan hydrochloride (CAMPTOSAR), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (ARA-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (ARA-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'-(trifluorometh-yl) propionanilide, Herceptin, anti-CD20 (Rituxan), interferon alpha, interferon beta, interferon gamma, interleukin 2, interleukin 4, interleukin 12, tumor necrosis factors, and radiation. Representative compounds used in cancer therapy further include cyclophosphamide, chlorambucil, melphalan, estramustine, iphosphamide, prednimustin, busulphan, tiottepa, carmustin, lomustine, methotrexate, azathioprine, mercaptopurine, thioguanine, cytarabine, fluorouracil, vinblastine, vincristine, vindesine, etoposide, teniposide, dactinomucin, doxorubin, dunorubicine, epirubicine, bleomycin, nitomycin, cisplatin, carboplatin, procarbazine, amacrine, mitoxantron, tamoxifen, nilutamid, and aminoglutemide.

The nutritional supplement component of the formulation can be any of a vitamin, mineral, essential fatty acid or fatty alcohol, essential metal, or botanical as described above which compensates for nutritional deficiencies associated with cancer treatment or which augments the activity of the chemotherapeutic agent.

Treatment of Other Diseases

Also provided herein are compositions and methods for the treatment or prevention of schizophrenia comprising administering to a patient a therapeutically effective amount of a multiple unit dosage form comprising, consisting essentially of, or consisting of an anti-psychotic such as olanzapine and a chromium complex, and a pharmaceutically acceptable vehicle.

The invention described herein further includes a composition and method for treating depression. The method includes identifying a subject suffering from depression and administering to said subject a therapeutically effective dose of a multiple unit oral formulation comprising an anti-depressant such as sertraline and a nutrient such as chromium, wherein the combination therapy results in a reduction in the symptoms of depression.

In addition to treating or preventing obesity, the compositions described herein can be administered to an individual to promote weight reduction of the individual. Conventional weight loss therapeutics can be formulated with a nutritional supplement coating to compensate for any nutritional depletion associated with weight loss treatment.

Veterinary and Livestock Uses

Compositions described herein can be administered to an animal or non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the compositions disclosed herein can be used to reduce the fat content of livestock to produce leaner meats. Alternatively, the compositions disclosed herein can be used to reduce the cholesterol content of eggs by administering the compounds to a chicken, quail, or duck hen. For non-human animal uses, the compositions disclosed herein can be administered via the animals' feed or orally as a drench composition.

Therapeutic/Prophylactic Administration and Compositions

Due to the activity of the compounds and compositions described herein, they are useful in veterinary and human medicine. As described above, the compounds and compositions described herein are useful for the treatment or prevention of cardiometabolic syndrome, aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, enhancing bile production,-enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

Provided herein are methods of treatment and prophylaxis of the conditions enumerated above by providing to a subject of a multiple unit dosage form having a therapeutically effective amount of a therapeutic agent and a nutritional supplement as disclosed herein. The mammal is an animal, including, but not limited to an animal such a cow, horse, sheep, pig, chicken, turkey, quail, cat, dog, mouse, rat, rabbit, guinea pig, etc., and most preferably a human.

The compositions disclosed herein are useful for methods for treating diabetes and its related pathologies, cardiovascular and related diseases, such as, for example, diabetes retinopathy, diabetes nephropathy, diabetes neuropathy, diabetes foot problems, diabetes infections and inflammations, diabetes with cardiovascular complications such as hypertrophy, hypertension, congestive heart failure, myocardial ischemia, ischemia reperfusion injuries in an organ, arrhythmia, and myocardial infarction. One embodiment is directed to a method of treating cardiovascular disease in a mammal by concurrently administering to the mammal a therapeutically effective amount of a combination of a compound suitable for use in methods described herein and a therapeutic cardiovascular compound such as chromium histidine or chromium complex as a multiple unit dosage form.

Other methods will be known to the skilled artisan and are within the scope described herein, including processes for preparing the formulations described above.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:
1. A dosage form for oral administration comprising:
an inner therapeutic agent core comprising a therapeutic agent, wherein the therapeutic agent core is located at the center of the dosage form;

a middle barrier layer disposed directly on and surrounding the inner therapeutic agent core; and an outer nutritional supplement layer disposed directly on and surrounding the middle barrier layer consisting of a nutritional supplement and one or more additional components selected from the group consisting of a pharmaceutically acceptable carrier, a sweetener, a flavoring agent, a coloring agent, a preservative and an excipient, and wherein the nutritional supplement is selected from the group consisting of biotin, choline, folate, niacin, pantothenic acid, riboflavin, thiamine, vitamin A, vitamin B6, vitamin B12, vitamin C, vitamin E, bromine, cobalt, copper, fluorine, germanium, iodine, iron, magnesium, manganese, molybdenum, potassium, selenium, silicon, zinc, calcium, phosphorous, sodium, sulfur, and vanadium, or combinations thereof.

2. The dosage form of claim 1, wherein the therapeutic agent is selected from the group consisting of analgesics, anesthetics, anxiolytics, anticonvulsants, antiemetics, bronchodilators, decongestants, anti-proliferatives, antibiotics, anti-virals, chemotherapeutics, immuno-suppressants, hormonal contraceptives, selective estrogen receptor modulators, fertility agents, and anti-pruritics, or combinations thereof.

3. The dosage form of claim 2, wherein the therapeutic agent is provided in a therapeutically effective amount.

4. The dosage form of claim 1, wherein the therapeutic agent is selected from anxiolytics, anticonvulsants, antiemetics, hormonal contraceptives, selective estrogen receptor modulators, and fertility agents, or combinations thereof.

5. The dosage form of claim 4, wherein the therapeutic agent is selected from anxiolytics, hormonal contraceptives, and fertility agents, or combinations thereof.

6. The dosage form of claim 5, wherein the therapeutic agent is selected from hormonal contraceptives and fertility agents.

7. The dosage form of claim 6, wherein the therapeutic agent is one or more hormonal contraceptives.

8. The dosage form of claim 6, wherein the therapeutic agent is one or more fertility agents.

9. The dosage form of claim 1, wherein the barrier layer is comprised of a controlled-release, delayed-release, sustained release, or enteric coating.

10. The dosage form of claim 1, wherein the nutritional supplement is provided in a therapeutically effective amount.

11. The dosage form for oral administration of claim 1, further comprising an outer coating.

12. A method of preventing and/or attenuating depletion of a nutrient caused by the co-administration of a therapeutic agent to an individual in need thereof, comprising:
identifying an individual presenting with nutrient depletion associated with the administration of a therapeutic agent; and
administering to the individual the dosage form of claim 1, wherein said therapeutic agent causes or exacerbates nutrient depletion, wherein said nutritional supplement prevents and/or attenuates said depletion; and wherein said nutrient is selected from the group consisting of biotin, choline, folate, niacin, pantothenic acid, riboflavin, thiamine, vitamin A, vitamin B6, vitamin B 12, vitamin C, vitamin E, bromine, cobalt, copper, fluorine, germanium, iodine, iron, magnesium, manganese, molybdenum, potassium, selenium, silicon, zinc, calcium, phosphorous, sodium, sulfur, and vanadium, or combinations thereof.

13. The method of claim 12, wherein said therapeutic agent is selected from anxiolytics, anticonvulsants, antiemetics, hormonal contraceptives, selective estrogen receptor modulators, and fertility agents, or combinations thereof.

14. The method of claim 12, wherein said therapeutic agent is selected from anxiolytics, hormonal contraceptives, and fertility agents, or combinations thereof.

15. The method of claim 12, wherein said therapeutic agent is selected from hormonal contraceptives and fertility agents.

16. The method of claim 12, wherein said therapeutic agent is one or more hormonal contraceptives.

17. The method of claim 12, wherein said therapeutic agent is one or more fertility agents.

18. The method of claim 12, wherein said nutritional supplement prevents said nutrient depletion.

19. The method of claim 12, wherein said nutritional supplement attenuates said nutrient depletion.

20. A dosage form for oral administration comprising:
an inner therapeutic agent core comprising a therapeutic agent, wherein the therapeutic agent comprises an immunosuppressant;
a middle barrier layer disposed over and surrounding the inner therapeutic agent core, wherein the middle barrier layer is comprised of an enteric coating; and
an outer nutritional supplement layer disposed over and surrounding the middle barrier layer consisting of biotin and one or more additional components selected from the group consisting of a pharmaceutically acceptable carrier, a sweetener, a flavoring agent, a coloring agent, a preservative and an excipient.

21. A dosage form for oral administration comprising:
an inner therapeutic agent core comprising a therapeutic agent;
a middle barrier layer disposed over and surrounding the inner therapeutic agent core; and
an outer nutritional supplement layer disposed over and surrounding the middle barrier layer consisting of a nutritional supplement and one or more additional components selected from the group consisting of a pharmaceutically acceptable carrier, a sweetener, a flavoring agent, a coloring agent, a preservative and an excipient, and wherein the nutritional supplement is selected from the group consisting of biotin, choline, folate, pantothenic acid, riboflavin, thiamine, vitamin A, vitamin B6, vitamin B12, vitamin C, vitamin E, bromine, cobalt, copper, fluorine, germanium, iodine, iron, magnesium, manganese, molybdenum, potassium, selenium, silicon, zinc, calcium, phosphorous, sodium, sulfur, and vanadium, or combinations thereof.

22. A dosage form for oral administration comprising:
an inner therapeutic agent core comprising a therapeutic agent, wherein the therapeutic agent core is located at the center of the dosage form;
a middle barrier layer disposed directly on and surrounding the inner therapeutic agent core; and
an outer nutritional supplement layer disposed directly on and surrounding the middle barrier layer consisting of a nutritional supplement, and wherein the nutritional supplement is selected from the group consisting of biotin, choline, folate, niacin, pantothenic acid, riboflavin, thiamine, vitamin A, vitamin B6, vitamin B12, vitamin C, vitamin E, bromine, cobalt, copper, fluorine, germanium, iodine, iron, magnesium, manganese, molybdenum, potassium, selenium, silicon, zinc, calcium, phosphorous, sodium, sulfur, and vanadium, or combinations thereof.

* * * * *